US006953882B2

(12) United States Patent
Martinez Force et al.

(10) Patent No.: US 6,953,882 B2
(45) Date of Patent: Oct. 11, 2005

(54) OIL FROM SEEDS WITH A MODIFIED FATTY ACID COMPOSITION

(75) Inventors: Enrique Martinez Force, Sevilla (ES); Begona Perez Vich, Sevilla (ES); Jose M. Fernandez Martinez, Cordoba (ES); Rafael Garces, Sevilla (ES)

(73) Assignee: Consejo Superior de Investigaciones Cientificas, Sevilla (ES)

( * ) Notice: Subject to any disclaimer, the term of this patent is extended or adjusted under 35 U.S.C. 154(b) by 244 days.

(21) Appl. No.: 10/076,759

(22) Filed: Feb. 14, 2002

(65) Prior Publication Data

US 2002/0183533 A1 Dec. 5, 2002

Related U.S. Application Data

(62) Division of application No. 09/326,500, filed on Jun. 4, 1999, now Pat. No. 6,348,610.

(51) Int. Cl.[7] ................................................ A01H 5/00
(52) U.S. Cl. ...................................... 800/322; 800/264
(58) Field of Search ............................... 800/322, 264, 800/270

(56) References Cited

U.S. PATENT DOCUMENTS 4,627,192 A    12/1986    Fick

FOREIGN PATENT DOCUMENTS

| WO | WO 95/20313 | 8/1995 |
| WO | WO 96/39804 | 12/1996 |
| WO | WO 97/12047 | 4/1997 |

OTHER PUBLICATIONS

Garces, R., and M. Mancha, "One–Step Lipid Extraction and Fatty Acid Methyl Esters Preparation From Fresh Plant Tissues," *Analytical Biochemistry* 211:139–143, 1993.

Gunstone, F.D., et al., *The Lipid Handbook*, 2d ed., Chapman and Hall, London, 1994, pp. 101–102 and 118–119.

Nestel, P., et al., "Effects of Increasing Dietary Palmitoleic Acid Compared with Palmitic and Oleic Acids on Plasma Lipids of Hypercholesterolemic Men," *J. Lipid Research* 35:656–662, 1994.

*Primary Examiner*—Elizabeth F. McElwain
(74) *Attorney, Agent, or Firm*—Christensen O'Connor Johnson Kindness PLLC

(57) ABSTRACT

Sunflower seeds having an oleic acid content of more than 5% and less than 65%, a palmitic acid content of more than 20% and less than 40%, a stearic acid content of more than 3% and less than 15%, and a palmitoleic acid content less than 4%, all based on the total fatty acid weight, are disclosed, together with methods of obtaining the sunflower seeds.

3 Claims, No Drawings

OIL FROM SEEDS WITH A MODIFIED FATTY ACID COMPOSITION

CROSS-REFERENCE TO RELATED APPLICATION

This application is a division of U.S. application Ser. No. 09/326,500, filed Jun. 4, 1999, now U.S. Pat. No. 6,348,610, priority from the filing date of which is hereby claimed under 35 U.S.C. § 120.

OBJECT OF THE INVENTION

The present invention relates to oil from seeds having a palmitic acid content of more than 20% and less than 40% by weight based upon the total fatty acid content, while the palmitoleic acid content is less than 4% based upon the total fatty acid content and the asclepic (n-7 isomer of oleic acid) acid content is less than 4%.

In particular, the invention relates to sunflower oil comprising an oleic acid content of more than 5% and less than 65% by weight based upon the total fatty acid content, a linoleic acid content less than 65% by weight based upon the total fatty acid content, a palmitic acid content of more than 20% and less than 40% by weight based upon the total fatty acid content, a stearic acid content of more than 3% and less than 15% based upon the total fatty acid content, while the palmitoleic acid content is less than 4% upon the total fatty acid content and the asclepic acid content is less than 4% based upon the total fatty acid content.

The oil of the invention may be used for applications in the food industry which require high thermostability or plastic fats.

BACKGROUND OF THE INVENTION

Sunflower is generally cultivated for obtaining oil which has saturated fatty acids (palmitic and stearic) and unsaturated fatty acids (oleic and linoleic), the stearic acid content is always less than 10% (Gunstone, F. D. et al. "The lipid handbook"; Chapman and Hall 1986), normally comprised between 3% and 7. In relation with the unsaturated fatty acids there are two different kinds of sunflower seeds: the normal sunflower which has a linoleic acid content between 50% and 70% (Knowles, P. F.

"Recent advances in oil crops breeding"; ROCS Proceedings 1988) and the high oleic sunflower which has 2–10% of linoleic acid and 75–90% of oleic acid (Soldatov, K.l. "Chemical mutagenesis in sunflower breeding "; Int. Proc. 7th Intern. Sunflower Conference, 352–357, 1976). Another high oleic sunflower line has been referred by Fick (US-B1-4627192), with oleic acid content of approximately 80 %

Referring to saturated fatty acids, high stearic sunflower lines are disclosed in WO 95/20313.

Further references to sunflower lines with high palmitic acid content are WO 96/39804 and Retske et al. "Triacylglycerol composition and structure in genetically modified sunflower and soybean oils"; JAOCS 74, 989–998 (1997), European Patent Appl. 98201871.5 and Nikolova et al. "Gametocidal effect of gibberellic acid (GA3) on biochemical characteristics of sunflower seeds" Helia, 15, Nr. 17, 45–50, (1992). In all these lines, the increase in palmitic acid implies higher palmitoleic acid content, always over 4%, and where the two "cis" isomers n-7 octadecenoic acid (asclepic) and n-9 octadecenoic (oleic) acid have been analyzed, an increase in the n-7 (asclepic acid) isomer has been observed.

Table 1 shows the fatty acid composition for all this indicated sunflower oil varieties.

TABLE 1

| Reference | Line | Fatty acids composition (%) | | | | | | | | |
|---|---|---|---|---|---|---|---|---|---|---|
| | | 16:0 | 16:1 | 16:2 | 18:0 | 18:1 | 18:1A | 18:2 | 20:0 | 22:0 |
| Gunstone | Normal | 6 | — | — | 5 | 18 | — | 68 | — | 1 |
| | Oleic | 5 | — | — | 4 | 88 | — | 2 | — | 1 |
| Nikolova, 1992 | | 29 | 5 | * | 2 | 9 | * | 55 | * | * |
| Reske, 1997 | | 25 | 6 | * | 3 | 60 | * | 4 | — | 2 |
| | | 27 | 4 | * | 3 | 17 | * | 47 | — | 1 |
| | CAS-5 | 31 | 5 | 1 | 3 | 5 | 6 | 47 | — | 1 |
| | CAS-12 | 30 | 7 | — | 2 | 52 | 4 | 3 | — | 2 |

* These fatty acids were not determined in those papers.
— = Traces.

The saturated fatty acid content of an oil is directly related with the physical and chemical characteristics thereof. In case that said content is sufficiently high, the oil can be a solid at room temperature like some animal fats. Normal sunflower oil is always a liquid under said conditions. In the food industry like for the production of confectionery or margarine; animal fats or hydrogenated vegetable fats are usually used because a solid or semisolid product is required. By means of hydrogenation unsaturated fatty acids are converted into saturated fatty acids. Animal fats as well as hydrogenated fats are not very recommendable from a nutritional point of view (Chow, C. K. "Fatty acids in food and their health implications", Dekker, N.Y. , 1992). Animal fats have a relatively high cholesterol content. Too much cholesterol in the diet may be detrimental to the health. Therefore animal fats have been substituted in the last years by hydrogenated vegetable fats which do not contain cholesterol.

However, said hydrogenated fats present another problem derived from the hydrogenation process. In said process positional isomerization (shift or double bonds) and stereochemical transformations (formation of "trans" isomers) take place. Isomers are produced in an amount of up to 30%–50% of the total fatty acids amount. These isomers are not very healthy from a nutritional point of view (Wood, R. "Biological effects of geometrical and positional isomers of monounsaturated fatty acids in humans", Dekker, N.Y. 1990; Willet, W. C. & Ascherio, A. , "Trams Fatty Acids: Are the effects only marginal?", American Journal of Public Health, Vol. 84,5, 1994). Therefore, the use of hydrogenated fats in the food industry should be avoided.

As previously referred, the increase in palmitic acid implies higher palmitoleic acid contents, always over 4% (see WO 96/39804). These oils are useful for food industry which requires high thermostability, but the presence of the indicated palmitoleic acid contents is still undesirable. Studies carried out on macadamia oil, which has 4% palmitoleic acid content indicate a negative effect on plasmatic cholesterol when compared with palmitic and oleic (Nestel et al., "Effects of increasing dietary palmitoleic acid compared with palmitic and oleic acids on plasma lipids of hypercholesterolemic men", Journal Lipid Research, vol. 35, pp. 656–662, 1994). This oil has also higher asclepic acid contents (n-7 isomer of octadecanoic acid) than other normal sunflower oil that have 0.6 % or other vegetable oils, like soybean or rape which have 0.8 and 0.9 % respectively (Mukherjee K. D. and Kiewitt I., "Formation of (n-9) and (n-7) cis-monounsaturated fatty acids in seeds of higher plants", Planta, vol. 149, pp. 461–463.

It can be concluded that an oil having higher palmitic and stearic acid contents than normal sunflower oil, but maintaining reduced levels of palmitoleic and asclepic acids would meet all the requirements for food industry implying high thermostability and plasticity to be spread.

BRIEF DESCRIPTION OF THE INVENTION

The present invention relates to oil from seeds comprising an oleic acid content of more than 5% and less than 65% by weight based upon the total fatty acid content, a linoleic acid content of more than 1% and less than 65% by weight based upon the total fatty acid content, a palmitic acid content of more than 20% and less than 40% by weight based upon the total fatty acid content, a stearic acid content of more than 3% and less than 15% based upon the total fatty acid content, while the palmitoleic acid content is less than 4% based upon the total fatty acid content and the asclepic acid content is less than 4% based upon the total fatty acid content. Preferably, the palmitoleic acid content is less than 3% based upon the total fatty acid content and the asclepic acid content is less than 3% o based upon the total fatty acid content.

The oil from seeds according to the present invention has an oleic acid content which is at least 40% by weight based upon the total fatty acid content and a linoleic acid content which is less than 18%. The total level of saturated fatty acids in the oil is at least 26%, preferably higher than 35%, most preferably higher than 45% based upon the total fatty acids content.

In reference to the position of the fatty acid groups in the triacylglycerols (TAG), the oil of the invention has least than 10%, preferably least than 5% by weight of the saturated fatty acid groups in the 2 position of the TAGs.

The invention in particular relates to sunflower oil, which is extracted from sunflower seeds obtained by crossing sunflower seeds of the mutant sunflower line IG-1297M deposited on 20 Jan. 1998 with ATCC under deposit accession number ATCC-209591 with the mutant sunflower line CAS-3, deposited on 14 Dec. 1994 with the ATCC under deposit accession number ATCC-75968.

The invention further relates to sunflower seeds comprising a sunflower oil with a fatty acid composition as referred herein above and to a method for preparing sunflower seeds, comprising the steps of a) crossing sunflower seeds of the mutant sunflower line IG-1297M deposited on 20 Jan. 1998 with ATCC under deposit accession number ATCC-209591 with the mutant sunflower line CAS-3, deposited on 14 Dec. 1994 with the ATCC under deposit accession number ATCC-75968.

b) self-pollinating F1 progeny plants of step a) for at least two generations to produce inbred plants.

c) selecting from the progeny of step b) plants with seeds containing an oil having a palmitic acid higher than 20%, palmitoleic acid content of less than 4% and an asclepic acid content of less than 3%.

d) collecting progeny seeds from step c) and optionally e) repeating the cycle of culturing, selection and collection of seeds.

The sunflower oil, prepared by extracting said sunflower seeds may be used in roasting, cooking, frying, baking and in general at high temperature conditions which constitute heating by any means at temperatures of at least 70° C. Said oil may also be used in the production of edible fats or fat mixtures, as well as in confectionery and bakery.

DETAILED DESCRIPTION OF THE INVENTION

The method for preparing seeds with a modified fatty acid composition comprises mutagenesis of seeds with a suitable mutagenic agent. The mutagenesis will produce inheritable genetic changes in the DNA of the seeds. According to the invention it was possible after several different experiments to select some treatments that produce a high number of genetic modifications in the genes that control the seed fatty acid biosynthesis. These treatments comprise the use of sodium azide or an alkylating agent, like ethyl methane sulfonate. Of course any other mutagenic agent having the same or similar effects may also be used.

Then, the next seed generation was analyzed with a new methodology described in Garces, R. and Mancha, M. "One step lipid extraction and fatty acid methyl esters preparation from fresh plant tissues"; Analytical Biochemistry, 211:139–143, 1993. This allowed for the detection of seeds with modifications in the composition of any fatty acid. Selected seeds showing a desirable fatty acid composition have been cultivated to the fifth generation showing that this new genetic trait is inheritable and stable and independent of growth conditions. In the method of the invention the parent seeds are for example treated during 2 hours at room temperature with a solution of 70 mM ethyl methane sulfonate in water, or during 2 hours at room temperature with a solution of 2 mM sodium azide in water. Further, the mutation and selection steps may be followed by conventional plant improvement techniques thus leading to seeds having a desirable fatty acids content. The seeds of the invention may be subjected to one or more further mutation treatments. Another way of obtaining mutagenized seeds consists of submitting the seeds to X-rays action, growing the treated seeds, self-pollination and further analysis of the fatty acid content. Further growing and selection steps will lead to plants with the desired new character fixed.

Sunflower oil having the desirable fatty acid composition may be prepared by extraction from sunflower seeds of the invention in any manner known to the person skilled in the art. Such extraction methods are well known and for example described in "Bailey's industrial oil and fat products", Vol. 2, Chapter3; 4th Edition, John Wiley and Sons, New York (1982).

By the referred methods seeds and oil having high stearic acid and high palmitic acid content can be obtained. High palmitic acid content normally implies high palmitoleic acid content which is not desirable from a nutritional point of view, as previously indicated. However, biochemical research on sunflower mutant lines indicates that the high stearic mutant has less stearoyl desaturase activity over palmitoyl-ACP than other sunflower mutant lines. Crossing a high stearic line (CAS-3) with a high palmitic line (CAS-12) and selecting in search of different fatty acid compositions, it turned out that in certain F2 generations that amounts of palmitoleic and asclepic acid decreased. Thus, the desaturation of palmitic into palmitoleic in the high palmitic acid mutants could be reduced introducing the stearoyl desaturase enzimatic activity of the high stearic mutant lines.

The invention is further illustrated by means of the following examples:

EXAMPLE 1

Sunflower seeds RDF-1-532 (Sunflower Collection of Instituto de Agricultura Sostenible, CSIC, Cordoba, Spain) which have 4% to 7% stearic acid content were mutagenized with a solution of 70 mM of ethyl methane sulfonate (EMS) in water. The treatment was performed at room temperature during 2 hours while shaking (60 rpm). After mutagenesis the EMS solution was discarded and seeds were washed during 16 hours under tap water.

Treated seeds were germinated in the field and plants were self-pollinated. The seeds collected from these plants were used to select new sunflower lines with modifications in the fatty acid composition. By using the method of Garces, R. and Mancha, M, referred to herein above, the seed fatty acid composition was determined by gas-liquid chromatography, after converting the fatty acids into their corresponding methyl esters.

A first plant with 9 to 17% stearic acid content in the oil was selected. The progeny was cultivated for five generations wherein the stearic acid content increased and the new genetic trait became stable fixed in the genetic material of the seed. This line is called CAS-3. A selected sample of this line was analyzed resulting in a stearic acid content of 26% (Table 2). The minimum and the maximum stearic acid content of the line were 19 and 35% respectively. The stearic acid content of oil extracted from seeds from this cell line may thus lie between 19 and 35%.

EXAMPLE 2

Sunflower seeds RDF-1-532 were mutagenized with sodium azide, at a concentration of 2 mM in water. The treatment was performed at room temperature during two hours while shaking. Then the mutagenesis solution was discarded and seeds were washed during 16 hours with tap water.

Seeds were planted in the field and plants were self-pollinated. Seeds from these plants were collected, and the fatty acid composition was determined by gas-liquid chromatography, after converting the fatty acids into their corresponding methyl esters using the method described in Example 1. Seeds from a plant having around 10% stearic acid in the oil were selected and cultivated for five generations. During this procedure the stearic acid content was increased and the new genetic trait fixed. This line is called CAS-4. A selected sample of this line was analyzed resulting in a stearic acid content of 16.1%. The minimum and the maximum values were 12 and 19% respectively.

EXAMPLE 3

5000 dry sunflower seeds were mutagenized by treatment with X-rays 300 cGy/min, beam 200 kV, 18 mA-1 and dose 160 Gy with a Siemens Stabilipan (Erlangen, Germany), seeds were grown in spring in the field. Self-pollinated plants were collected individually and seeds analyzed for their fatty acid content. Seeds with at least three times more saturated fatty acid content that the standard deviation for the specific fatty acid were selected and successively grown until the new character was fixed. Several putative new mutant lines were selected by this method. After further selection for triacylglycerol composition line IG-1297M was selected.

EXAMPLE 4

Sunflower plants were grown from the sunflower seeds of CAS-3 according to Example 1. Sunflower plants were grown from the sunflower seeds of IG-1297M according to Example 3.

The lines were crossed. The plants were assisted by artificial pollination in order to ensure adequate seed production occurred. The F1 was produced on the IG-1297M and harvested. F2 IG-1297M parent seeds with a high oleic acid background having more than 20% palmitic acid and less than 4% of both palmitoleic and asclepic acid were selected.

Although the oil produced by these selected lines is the oil of the present invention, the level of production is limited, therefore fixed inbred. lines evidencing seeds with these oil profiles are desirable. These homozygous fixed high oleic, high palmitic, low palmitoleic, low asclepic inbred lines can then be crossed to form hybrid seed, which will produce F2 seed evidencing the desired oil traits of the present invention. Toward this end the F1 seeds were planted and produced plants were selfed in isolated conditions and F2 seed was produced. The F2 seed, called QQ-3598-M was tested for the four traits: high palmitic, high oleic, low palmitoleic, and asclepic. The remaining portion of the seeds evidencing these traits was employed to grow plants to form F3 seed. The selfing and screening and selection process is repeated to develop the fixed homozygous QQ-3598-M line, having the following fatty acid profile: C16:0 30.5%; C18:0 9.6%; C18:1 47.2%; C18:2 6.7%; C16:1 2.1%; C18:1A 1.1%, and least than 1% of other minor fatty acids.

Once the trait infixed, similar QQ-3598-M lines can cross to form hybrid seed having the desired traits. This characteristic fatty acid profile is an inheritable trait and is fairly independent from the growing conditions.

What is claimed is:

1. Sunflower seeds comprising a sunflower oil having:

an oleic acid content of more than 5% and less than 65% by weight based upon the total fatty acid content, a linoleic acid content of more than 1% and less than 65% by weight based upon the total fatty acid content, a palmitic acid content of more than 20% and less than 40% by weight based upon the total fatty acid content, a stearic acid content of more than 3% and less than 15% based upon the total fatty acid content, wherein the palmitoleic acid content is less than 4% based upon the total fatty acid content, and the asclepic acid content is less than 4% based upon the total fatty acid content.

2. Sunflower seeds of claim 1 wherein the palmitoleic acid content is less than 3% based upon the total fatty acid content.

3. Method for preparing sunflower seeds as claimed in claim 1, comprising the steps of:

a) crossing the mutant sunflower line IG-1297M deposited on 20 Jan. 1998 with ATCC under deposit accession number ATCC-209591 with the mutant sunflower line CAS-3, deposited on 14 Dec. 1994 with the ATCC under deposit accession number ATCC-75968, b) self-pollinating FL progeny plants of step a) for at least two generations to produce inbred plants, c) selecting from the progeny of step b) plants with seeds containing an oil having a palmitic acid content of more than 20%, a palmitoleic acid content of less than 4% and an asclepic acid content of less than 3%, d) collecting progeny seeds from step c), and optionally e) repeating the cycle of culturing, selection and collection of seeds.

* * * * *

UNITED STATES PATENT AND TRADEMARK OFFICE
CERTIFICATE OF CORRECTION

PATENT NO. : 6,953,882 B2
DATED : October 11, 2005
INVENTOR(S) : E. Martinez Force et al.

It is certified that error appears in the above-identified patent and that said Letters Patent is hereby corrected as shown below:

Column 1,
Line 57, "7." should read -- 7%. --.
Lines 60-61, do not paragraph "P.F.
"Recent advances....."".
Line 67, "80 %" should read -- 80 % or greater. --.

Column 2,
Lines 4-5, "Triacylg-
lycerol" should read -- Triacyl-
glycerol --.

Column 4,
Line 51, "Chapter3;" should read -- Chapter 3; --.

Column 6,
Line 19, "and asclepic." should read -- and low asclepic. --.
Line 56, "FL" should read -- F1 --.

Signed and Sealed this

Twenty-first Day of March, 2006

JON W. DUDAS
*Director of the United States Patent and Trademark Office*